United States Patent
Aksenov et al.

(10) Patent No.: US 12,385,811 B2
(45) Date of Patent: Aug. 12, 2025

(54) DEVICE AND METHOD FOR IN SITU SAMPLING OF VOLATILES FROM SURFACES

(71) Applicant: The Regents of the University of California, Oakland, CA (US)

(72) Inventors: Alexander Aksenov, La Jolla, CA (US); Pieter Dorrestein, La Jolla, CA (US); Alexey Melnik, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 320 days.

(21) Appl. No.: 17/641,386

(22) PCT Filed: Sep. 10, 2020

(86) PCT No.: PCT/US2020/050121
§ 371 (c)(1),
(2) Date: Mar. 8, 2022

(87) PCT Pub. No.: WO2021/050678
PCT Pub. Date: Mar. 18, 2021

(65) Prior Publication Data
US 2022/0341822 A1    Oct. 27, 2022

Related U.S. Application Data

(60) Provisional application No. 62/899,184, filed on Sep. 12, 2019.

(51) Int. Cl.
*G01N 1/22* (2006.01)
*B01D 53/14* (2006.01)
*G01N 1/40* (2006.01)

(52) U.S. Cl.
CPC ............... *G01N 1/22* (2013.01); *B01D 53/14* (2013.01); *G01N 1/405* (2013.01)

(58) Field of Classification Search
CPC .................... G01N 1/22; G01N 1/405
USPC ............................................. 73/863.11
See application file for complete search history.

(56) References Cited

U.S. PATENT DOCUMENTS

| | | | |
|---|---|---|---|
| 2,312,501 A * | 3/1943 | Stonehill | A61F 13/53713 604/375 |
| 5,899,856 A * | 5/1999 | Schoendorfer | A61B 5/4266 600/362 |
| 6,063,041 A * | 5/2000 | Flament | A61B 10/0064 600/573 |
| 6,214,095 B1 | 4/2001 | Logan et al. | |

FOREIGN PATENT DOCUMENTS

| | | |
|---|---|---|
| JP | S64-9337 A | 1/1989 |
| WO | 2006000748 A1 | 10/2006 |

OTHER PUBLICATIONS

PCT International Search Report and Written Opinion for PCT/US2020/050121, mailed, Dec. 15, 2020, (6 pages.).

* cited by examiner

*Primary Examiner* — Peter J Macchiarolo
*Assistant Examiner* — Rodney T Frank
(74) *Attorney, Agent, or Firm* — Eversheds-Sutherland (US) LLP

(57) ABSTRACT

A sampling manifold and method of use for detecting volatile compounds on a surface, such as skin, comprising an adhesive base layer and mesh defining a pouch for insertion of a removable sorbent patch.

20 Claims, 2 Drawing Sheets

DEVICE AND METHOD FOR IN SITU SAMPLING OF VOLATILES FROM SURFACES

CROSS REFERENCE TO RELATED APPLICATIONS

This application is a U.S. National Phase Application of PCT Application No. PCT/US2020/050121, filed on Sep. 10, 2020, which claims the priority benefit to U.S. Provisional Application No. 62/899,184, filed Sep. 12, 2019, the entire contents of which are incorporated herein by reference.

TECHNICAL FIELD

The present invention relates to in situ sampling of volatiles from surfaces.

BACKGROUND

Currently, some of the methods used for sampling volatile organic compounds (VOCs) from surfaces include cotton swabs, thermal desorption tubes, and direct probes with mobile GC-MS devices containing a thermal desorption trap. The efficiency of sampling varies between sampling methods and between adsorbent materials used. None of these methods though allow for high-volume low-cost sampling. All of them use GC/MS for analysis.

The current existing solutions for in situ sampling all possess substantial drawbacks that make them non-optimal for being conducted on a large scale and/or inexpensively. For example, one of the most popular solutions is solid-phase microextraction (SPME) from Supelco; however, it is relatively expensive and rather fragile, not allowing sampling contact sampling. Another solution, stir bar sorptive extraction (SBSE) from Gerstel, is more robust but is designed for liquid sampling and thus comes in form factor that is not convenient for biological sampling of gas-phase volatiles (e.g. on the skin surface or a leaf of a plant). Moreover, it is expensive and requires a designated sampler on a GC/MS instrument, which is very costly. Other solutions, such as sorbent capsules or pens (e.g., using Tenax sorbent) all require special handling that may not be ideal for inexperienced users. Further, they are either unsuitable for contact surface sampling or not suitable for in situ sampling at all (for example, sorbent pens solution by Entech Instruments). Thus, a solution that allows inexpensive in situ sampling is needed. The present invention is designed to fill the existing gap.

SUMMARY OF THE INVENTION

The invention provides a manifold and method of use that allows sampling of a surface using an appropriate sorbent patch. The design allows the user to quickly dispatch the manifold and collect the sampled sorbent before analysis of analytes of interest, such as volatile organic compounds.

In embodiments, the invention provides a sampling manifold for collecting volatile compounds comprising a base layer having a front side and a back side, wherein the base layer is inert and impermeable to fluids or gases and wherein the front side has an adhesive coating surrounding at least a portion of a central sorbent patch region.

In embodiments, the invention provides a sampling manifold further comprising a mesh layer having a periphery edge, a front side and a back side adhered along at least a portion of the periphery edge to the front side of the base layer in the central sorbent patch region and defining a pouch between the back side of the mesh layer and the front side of the base layer with an opening for removably retaining a sorbent patch between the mesh layer and the base layer, and wherein the mesh layer permits fluids and gases to flow therethrough.

In embodiments, the invention provides a sampling manifold further comprising a sorbent patch removably inserted into the pouch, wherein the patch adsorbs fluids, gases, and gas-phase volatile compounds. In embodiments, the invention provides a sampling manifold further comprising a protective cover removably applied to the front side of the mesh layer wherein the protective cover is inert and prevents fluids and gases from contacting the sorbent patch within the mesh layer pouch.

In embodiments, the invention provides that the sorbent patch is made of polydimethylsiloxane. In embodiments, the invention provides that the sorbent patch is flexible and sterile. In embodiments, the invention provides that the sorbent patch is made of carbon nano-fibers. In embodiments, the invention provides that the protective cover is made of polyvinyl.

In embodiments, the invention provides a method of manufacturing the sampling manifold, comprising inserting the sorbent patch into the pouch of the mesh layer, degassing the sorbent patch and mesh layer under heated vacuum conditions, and sealing the sorbent patch and mesh layer with the protective cover.

In embodiments, the invention provides a method of detecting volatile compounds from a surface of an object comprising: removing the protective layer of the sampling manifold; adhering the front side of the sampling manifold to the surface; removing the sampling manifold from the surface; removing the sorbent patch from the pouch; and detecting volatile compounds on the sorbent patch from the surface.

In embodiments, the invention provides a method of detecting volatile compounds from a surface in situ wherein the surface is the skin of a subject. In embodiments, the invention provides a method of detecting volatile compounds from a surface in situ wherein the surface is a plant. In embodiments, the invention provides a method of detecting volatile compounds from a surface in situ wherein the surface is an inanimate object.

DETAILED DESCRIPTION

Figure 1A:
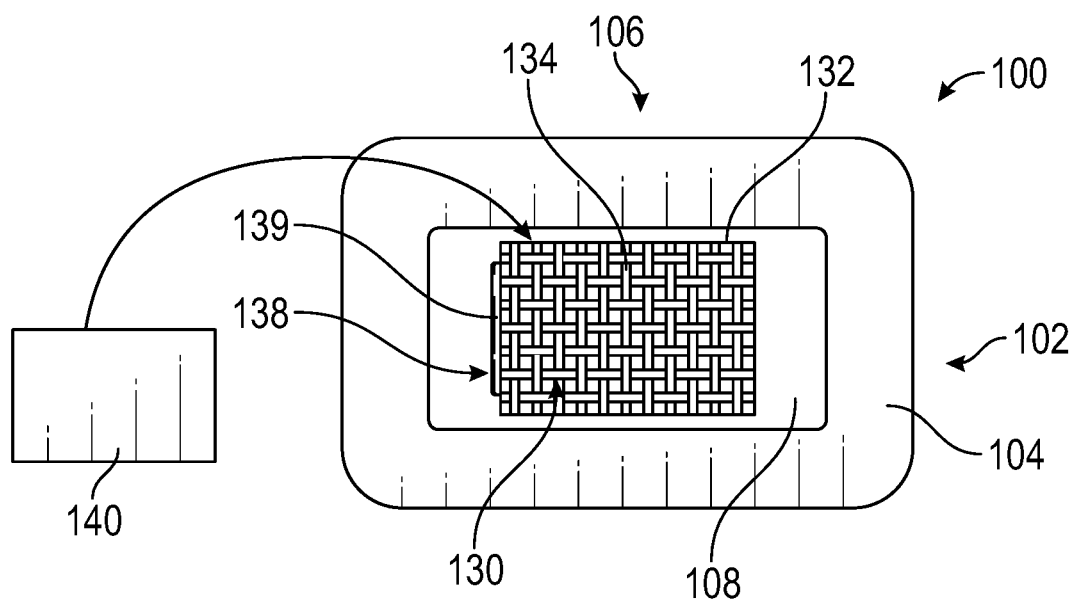
FIG. 1A shows a front view of the sampling manifold with the protective film removed.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms and any acronyms used herein have the same meanings as commonly understood by one of ordinary skill in the art in the field of the invention. Although any methods and materials similar or equivalent to those described herein can be used in the practice of the present invention, the exemplary methods, devices, and materials are described herein.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

It is understood that aspects and embodiments of the invention described herein include "consisting" and/or "consisting essentially of" aspects and embodiments.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Values or ranges may be also be expressed herein as "about," from "about" one particular value, and/or to "about" another particular value. When such values or ranges are expressed, other embodiments disclosed include the specific value recited, from the one particular value, and/or to the other particular value. Similarly, when values are expressed as approximations, by use of the antecedent "about," it will be understood that the particular value forms another embodiment. It will be further understood that there are a number of values disclosed therein, and that each value is also herein disclosed as "about" that particular value in addition to the value itself. In embodiments, "about" can be used to mean, for example, within 10% of the recited value, within 5% of the recited value, or within 2% of the recited value.

The invention provides a volatile compound sampling manifold that allows sampling of a surface using appropriate sorbent patch. The invention allows quickly dispatching the manifold for any user, then collecting the sampled sorbent patch, and shipping for analysis of analytes of interest, including volatile compounds.

In embodiments, the invention provides a sampling manifold for collecting volatile compounds. In embodiments, the sampling manifold comprises a base layer having a front side and a back side, wherein the base layer is inert and impermeable to fluids or gases and wherein the front side has an adhesive coating surrounding at least a portion of a central sorbent patch region.

In embodiments, the sampling manifold further comprises a mesh layer having a periphery edge, a front side and a back side adhered along at least a portion of the periphery edge to the front side of the base layer in the central sorbent patch region and defining a pouch between the back side of the mesh layer and the front side of the base layer with an opening for removably retaining a sorbent patch between the mesh layer and the base layer; and wherein the mesh layer permits fluids and gases to flow therethrough.

In embodiments, the sampling manifold further comprises a sorbent patch removably inserted into the pouch, wherein the patch adsorbs fluids, gases, and gas-phase volatile compounds. The sorbent patch is smaller in size that the pouch of the mesh layer.

In embodiments, the sampling manifold further comprises a protective cover removably applied to the front side of the mesh layer wherein the protective cover is inert and prevents fluids and gases from contacting the sorbent patch within the mesh layer pouch.

In embodiments, the invention provides that the sorbent patch is made of polydimethylsiloxane. In embodiments, the invention provides that the sorbent patch is flexible and sterile. In embodiments, the invention provides that the sorbent patch is made of carbon nano-fibers. In embodiments, the invention provides that the protective cover is made of polyvinyl.

In embodiments, the invention provides that the volatile compounds are volatile organic compounds. In embodiments, the invention provides that the volatile organic compounds are biologically generated compounds, such as isoprene, terpenes, piene isomers, sesquiterpenes or methanol. In embodiments, skin, such as human skin, emits the volatile organic compound. In embodiments, plants emit the volatile organic compounds. In embodiments, the invention provides that the volatile organic compounds are natural or man-made, such as, but not limited to: acetone, benzene, butanal, carbon disulfide, dichlorobenzene, ethanol, 2-butoxy ethanol, 2-phenoxy-ethanol, formaldehyde, toluene, xylene, trimethyl benzene, butylated hydroxytoluene, 3-phenoxy-1-propanol, alkanes, 1-butanol, 4-ethyl-morpholine, pyridine, C8-C12 aldehydes, nonanal, decanalacetic, ketones, 6-methyl-5-heptene-2-one, geranylacetone, squalene, lactic acid, dimethyl-sulphone, benzothiazole, hexyl salicylate, α-hexyl cinnamaldehyde, isopropyl palmitate, methoxy acetic acid dodecyl ester, benzothiazole, isoprenoids, terpenoids, acetaldehyde, methyl-ethyl-ketone, methyl-vinyl-ketone, sulfur compounds, and furanocoumarins. In embodiments, the volatile compounds for detection include, but are not limited to, ethanol, acetic acid, hexanal, 6-methyl-5-hepten-2-one, and nonanal, for example, and those recited in Dormont et al. "Human Skin Volatiles: A Review," J. Chem. Ecol., DOI 10.1007/s10886-013-0286-z (2013) or at gnps.ucsd.edu/ProteoSAFe/status.jsp?task=62ef713ba7ba4752935f7d355aaa63ca, both of which are incorporated by reference herein.

In embodiments, the invention provides a method of manufacturing the sampling manifold, comprising inserting the sorbent patch into the pouch of the mesh layer, degassing the sorbent patch and mesh layer under heated vacuum conditions, and sealing the sorbent patch and mesh layer with the protective cover. In embodiments, the invention provides that the degassing the sorbent patch and mesh layer under heated vacuum conditions can occur before inserting the sorbent patch into the pouch of the mesh layer.

In embodiments, the invention provides a method of detecting volatile compounds from a surface of an object comprising: removing the protective layer of the sampling manifold; adhering the front side of the sampling manifold to the sampling surface to allow volatile compounds to absorb onto the sorbent patch; removing the sampling manifold from the sampling surface; removing the sorbent patch from the pouch; and detecting volatile compounds on the sorbent patch from the surface. In embodiments, the detecting is performed by gas chromatography/mass spectrometry.

In embodiments, the invention provides a method of detecting volatile compounds from the surface wherein the surface is the skin of a human or animal. In embodiments, the invention provides a method of detecting volatile compounds from the surface wherein the surface is a plant, such as a leaf. In embodiments, the invention provides a method of detecting volatile compounds from the surface wherein the surface is an inanimate object, such as a table.

The invention is useful in large scale sampling of human skin, plants, and other biological or inert surfaces containing naturally occurring and man-made volatile compounds.

Figure 1B:
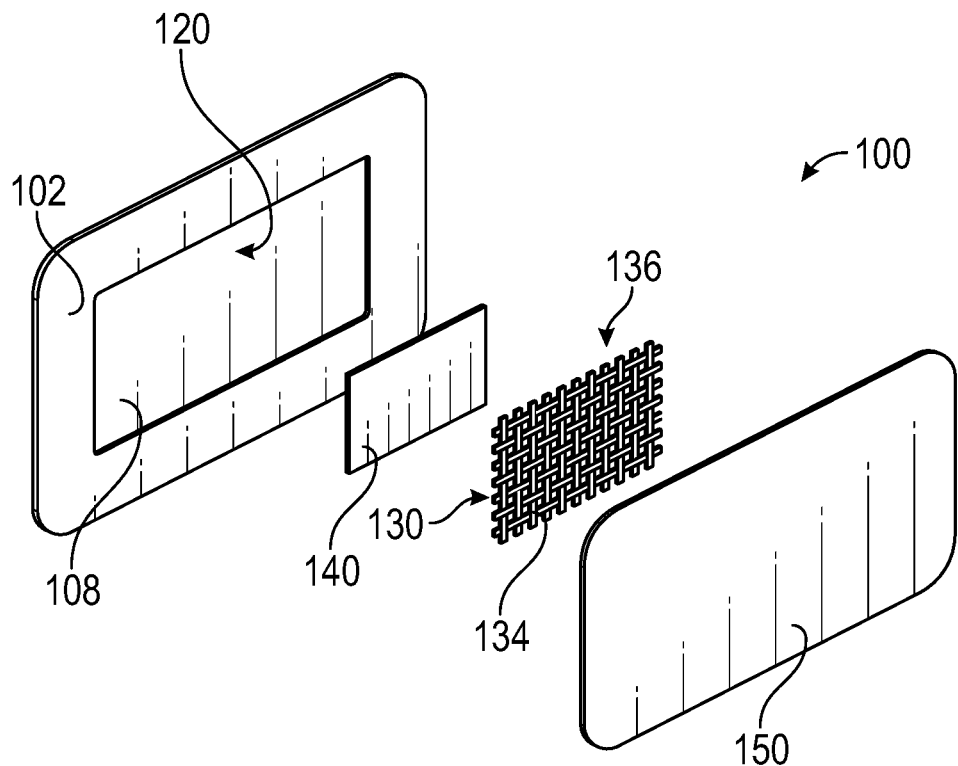
FIG. 1B shows an exploded view of the sampling manifold.
Figure 1C:
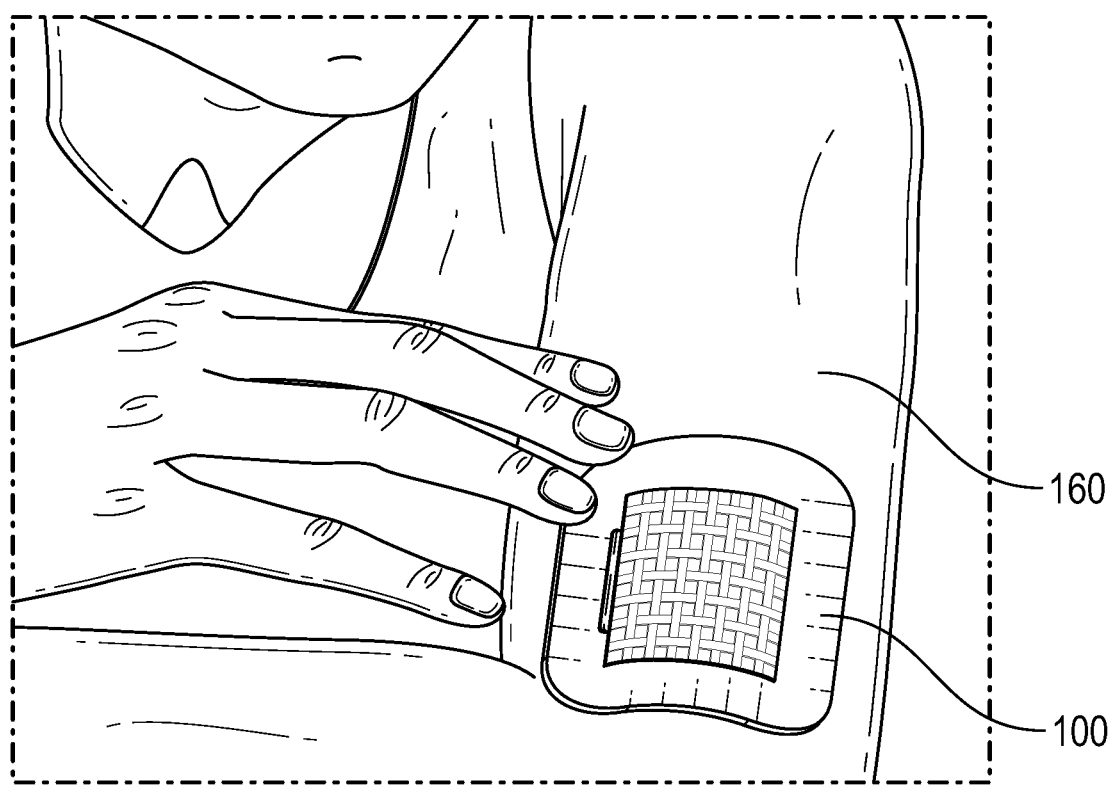
FIG. 1C shows an example of application of the sampling manifold.

The general schematics of one embodiment of the design is shown in FIGS. 1A-1C. FIG. 1A shows a front view of the sampling manifold 100 with the protective sealing film (not shown) removed. The sampling manifold 100 comprises a base layer 102 having a front side 104 and a back side 106, and an adhesive coating 108 on the front side 104 surrounding at least a portion of a central sorbent patch region 120 (shown in FIG. 1B). The base layer 102 is inert and impermeable to fluids or gases.

The manifold 100 further comprises a mesh layer 130 having a periphery edge 132, a front side 134 and a back side 136 (shown in FIG. 1B) adhered along at least a portion of the periphery edge 132 to the front side 104 of the base layer 102 in or around the central sorbent patch region 120. The adhesive coating 108 allows the mesh layer 130 to adhere along at least a portion of the periphery edge 132 to the front side 104 of the base layer 102. The mesh layer 130 thereby defines a pouch 138 between the back side 136 of the mesh layer 130 and the front side 104 of the base layer 102 with an opening 139 for removably retaining a sorbent patch 140 between the mesh layer 130 and the base layer 102.

The opening 139 for inserting, retaining and removing the sorbent patch 140 can be formed by a gap in the adhesive coating 108 surrounding other portions of the central sorbent patch region 120, or the opening 139 can be formed by creating a cut or slit in the mesh layer 130. The pouch opening 139 may be located anywhere on the mesh layer 130, for example on the left side, right side, top, or bottom, sized and shaped for insertion and removal of the sorbent patch 140. The mesh layer 130 permits fluids and gases containing volatile compounds to flow therethrough and be deposited on the sorbent patch 140.

The protective cover 150 is removably applied to the front side 134 of the mesh layer 130 with an adhesive wherein the protective cover is inert and prevents fluids and gases from contacting the sorbent patch 140 within the pouch 138 of the mesh layer 130. As shown in FIG. 1B, the protective cover 150 can encompass more than the mesh layer 130 and extend to cover the front side 104 (shown in FIG. 1A) of the base layer 102.

FIG. 1B shows an exploded view of the sampling manifold 100. The protective cover 150 is affixed for shipping and removed for sampling. The protective cover 150 is applied to the base layer 102 to protect the sorbent patch 140 and the mesh layer 130 and prevents fluids and gasses from contacting the sorbent patch 140 until the user is ready for sampling of volatile compounds.

FIG. 1C shows an example of application of the sampling manifold 100. The sampling manifold 100 may be removably affixed to a surface, such as human skin 160. In particular, the protective cover 150 is removed from the front side 134 of the base layer 102 to expose the sorbent patch 140 and the mesh layer 130. The adhesive coating 108 on the front side 104 of the base layer 102 can then be used to adhere the manifold 100 in situ to the surface to be tested for the presence of volatile compounds. The manifold 100 can remain on the sampling surface for a period of time ranging from 2 seconds to 10 hours, from 2 minutes to 6 hours, or from 1 hour to 6 hours. In the case of human skin, the best detection of VOCs was obtained with a manifold residence time of about three hours.

In embodiments, the invention provides methods of using the sampling manifold. In embodiments, the invention provides for method of volatile compound sampling, the method comprising: adhering the sampling manifold to a sampling surface; removing the adsorbent patch from the sampling manifold; and analyzing the adsorbent patch for an analyte of interest. In embodiments, the analyzing step comprises gas chromatography/mass spectrometry.

In embodiments, the invention further comprises the step of removing the sampling manifold from the sampling surface. In embodiments, the invention further comprises the step of inserting absorption residence times.

In embodiments, the sampling surface is human or animal skin, a plant, or an inanimate object. In embodiments, the analyte of interest is a volatile organic compound.

The sampling manifold can be made in different sizes, depending on the sampling area for different applications. In embodiments, the size of the sampling manifold ranges from 2 cm to 10 cm in width, and 2 cm to 10 cm in height. In embodiments, the size of the sorbent patch to be inserted into the manifold ranges from 0.5 cm to 5 cm in width, and 0.5 cm to 5 cm in height. In embodiments, the sorbent patch is about 1 cm×2 cm. Prior to deployment, such as at the manufacturing stage, the sorbent patch can be placed in the pouch in the middle of the mesh layer.

The invention provides that in certain embodiments, a further patch shield is adhered to the front side of the base layer, such that the back side of the sorbent patch is shielded from adhesive material. The front side of the sorbent is in contact with the thin mesh layer that holds the patch in place. The mesh layer forms a pouch that has a slit opening on a side through which the patch can be inserted.

A mesh layer material and sorbent patch material having a low volatile compound content that is suitable for particular applications, particularly gas chromatography or mass spectrometry (GC/MS) analysis, can be used. The mesh layer and sorbent patch can be made of a material that does not degass and is inert. For the mesh layer, when the patch is to be applied to a human or animal skin, the material can be non-toxic and non-irritant. For example, the mesh layer may comprise synthetic or natural fibers, such as untreated silk or cotton.

For the sorbent patch, polydimethylsiloxane (PDMS) is a suitable material for sampling of biological systems as it is non-toxic, inert, flexible and does not degrade or crumble during sampling. Further examples of materials for the sorbent patch include charcoal and polydivinyl benzene. Other, carbon-based sorbents can also be used, such as Tenax carbon nano-fibers, depending on the technique for analysis, such as GC/MS, where when the patch is heated, the volatiles are desorbed and injected into the instrument for analysis. However, any sorbent material that can be made into a non-brittle, flexible, sheet form (or engrafted as a layer on a sheet) can be used to form the sorbent patch. The sorbent patch can be re-heated for cleaning and reused to further reduce cost. Appropriate analytical techniques other than GC/MS can also be used for the analysis.

In one embodiment, a hydrophobic membrane sorbent patch is provided. By hydrophobic, it is meant in the context of the present invention that the membrane prevents the passage of fluid phase but permits the escape of vapor phase of volatile components. These hydrophobic membranes can also be referred to herein as gas permeable membranes. Alternatively, a hydrophilic membrane sorbent patch layer is provided. By hydrophilic, it is meant in the context of the present invention that the membrane or layer permits the passage of both liquid and vapor phases. Such hydrophilic layers can be referred to herein as liquid permeable membranes. In some embodiments, a hydrophobic membrane sorbent patch and a hydrophilic membrane sorbent patch are provided.

In embodiments, a liquid pre-treatment may be desired on the sorbent patch to stabilize or adhere the volatile organic compounds thereto. Whether a pre-treatment is used depends on the sorbent patch material. For example, if the sorbent patch comprises PDMS, the sorbent patch may be soaked in isopropanol or other solvent, before it is vacuum heated for initial degassing. The solvent soak removes dust from the manufacturing process. However, some sorbent patch materials do not require pre-treatment by solvent soaking. In embodiments of the invention, the sorbent patch may be supplied already clean and ready to use.

Degassing the sorbent patch can occur as a pre-treatment prior to sampling the volatile compound, as well as after sampling to release the volatile compound(s) from the sorbent patch for analysis. The heating time and temperature for degassing the sorbent patch depends on the sorbent material, as routinely determined by the user. If the sorbent patch insert comprises PDMS, the degassing heating temperature is between about 150° C. and up to about 250° C., above which PDMS begins to degrade. In some embodiments, the patch is heated to between 190° C. to 200° C. In embodiments, the time required for heating inversely depends on the temperature. In embodiments, the heating time for 200° C. degassing is approximately 10-15 minutes.

These exemplary embodiments and additional embodiments will be apparent to one of skill in the art upon a review of the present specification, drawings and claims.

What is claimed is:

1. A sampling manifold comprising:
   i. a base layer having a front side and a back side, wherein the base layer is inert and impermeable to fluids or gases and wherein the front side has an adhesive coating;
   ii. a mesh layer having a periphery edge, a front side and a back side adhered along at least a portion of the periphery edge to the front side of the base layer in the central sorbent patch region and defining a pouch between the back side of the mesh layer and the front side of the base layer with an opening for removably retaining a sorbent patch between the mesh layer and the base layer; and wherein the mesh layer permits fluids and gases to flow therethrough;
   iii. a sorbent patch removably inserted into the pouch, wherein the patch adsorbs fluids, gases, and gas-phase volatile compounds; and
   iv. a protective cover removably applied to the front side of the mesh layer wherein the protective cover is inert and prevents fluids and gases from contacting the sorbent patch within the mesh layer pouch;
   wherein a back side of the sorbent patch is adhered to the adhesive coating; and
   wherein, upon removal of the protective cover, the adhesive coating is adherable to a surface such that fluids, gases, and gas-phase volatile compounds from the surface are adsorbed by the sorbent patch.

2. The sampling manifold of claim 1, wherein the sorbent patch is made of polydimethylsiloxane.

3. The sampling manifold of claim 1, wherein the sorbent patch is flexible and sterile.

4. The sampling manifold of claim 1, wherein the sorbent patch is made of carbon nano-fibers.

5. The sampling manifold of claim 1, wherein the protective cover is made of polyvinyl.

6. The sampling manifold of claim 1, wherein the sorbent patch has been produced to reduce volatile compounds by degassing under heated vacuum conditions and sealed with the protective cover.

7. The sampling manifold of claim 1, wherein the opening for inserting, retaining and removing the sorbent patch is formed by a gap in the adhesive coating surrounding other portions of the central sorbent patch region.

8. The sampling manifold of claim 1, wherein the opening for inserting, retaining and removing the sorbent patch is formed by a slit in the mesh layer.

9. The sampling manifold of claim 1, further comprising a patch shield adhered to the front side of the base layer in the central sorbent patch region, such that the back side of the sorbent patch is shielded from adhesive material on the front side of the base layer.

10. A method of detecting volatile compounds from a surface of an object with the sampling manifold of claim 1, comprising removing the protective layer from the base layer; adhering the front side of the base layer to the surface; removing the base layer from the surface; removing the sorbent patch from the pouch; and detecting volatile compounds on the sorbent patch from the surface.

11. The method of claim 10, wherein the surface is skin.

12. The method of claim 10, wherein the surface is a plant.

13. The method of claim 10, wherein the surface is an inanimate object.

14. The method of claim 10, wherein the detecting is performed by gas chromatography/mass spectrometry.

15. A method of volatile compound sampling, the method comprising:
   i. adhering the sampling manifold of claim 1 to a sampling surface;
   ii. removing the adsorbent patch from the sampling manifold; and
   iii. analyzing the adsorbent patch for an analyte of interest.

16. The method of claim 15, further comprising the step of removing the sampling manifold from the sampling surface.

17. The method of claim 15, further comprising the step of inserting absorption residence times.

18. The method of claim 15, wherein the sampling surface is human or animal skin, a plant or an inanimate object.

19. The method of claim 15, wherein the analyte of interest is a volatile organic compound.

20. The method of claim 15, wherein the analyzing step comprises gas chromatography/mass spectrometry.

* * * * *